(12) United States Patent
Cunliffe et al.

(10) Patent No.: US 11,419,617 B2
(45) Date of Patent: Aug. 23, 2022

(54) SURGICAL APPARATUS

(71) Applicant: Orthomed (UK) Limited, Yorkshire (GB)

(72) Inventors: Mark Cunliffe, Huddersfield (GB); Neil James Burton, Axbridge (GB)

(73) Assignee: Orthomed (UK) Limited, Yorkshire (GB)

( * ) Notice: Subject to any disclaimer, the term of this patent is extended or adjusted under 35 U.S.C. 154(b) by 329 days.

(21) Appl. No.: 16/507,878

(22) Filed: Jul. 10, 2019

(65) Prior Publication Data

US 2019/0328407 A1    Oct. 31, 2019

Related U.S. Application Data

(62) Division of application No. 14/812,676, filed on Jul. 29, 2015, now abandoned.

(30) Foreign Application Priority Data

Jul. 29, 2014   (GB) .................................... 1413387

(51) Int. Cl.
| | | |
|---|---|---|
| *A61B 17/88* | (2006.01) | |
| *A61B 17/17* | (2006.01) | |
| *A61B 17/80* | (2006.01) | |
| *A61B 17/15* | (2006.01) | |
| *A61B 17/56* | (2006.01) | |
| *A61B 17/68* | (2006.01) | |

(52) U.S. Cl.
CPC ........ *A61B 17/1728* (2013.01); *A61B 17/151* (2013.01); *A61B 17/8004* (2013.01); *A61B 2017/564* (2013.01); *A61B 2017/681* (2013.01)

(58) Field of Classification Search
CPC combination set(s) only.
See application file for complete search history.

(56) References Cited

U.S. PATENT DOCUMENTS

| | | |
|---|---|---|
| 6,007,535 A | 12/1999 | Rayhack et al. |
| 2008/0114370 A1 | 5/2008 | Schoenefeld |
| 2009/0254126 A1* | 10/2009 | Orbay ................ A61B 17/1728 606/282 |

FOREIGN PATENT DOCUMENTS

| | | |
|---|---|---|
| EP | 0995403 A1 | 4/2020 |
| WO | 2012158253 A1 | 11/2012 |
| WO | 2013065883 A1 | 5/2013 |

* cited by examiner

*Primary Examiner* — Sameh R Boles
(74) *Attorney, Agent, or Firm* — Quinn IP Law (57) ABSTRACT

A surgical apparatus includes a combination of a drill guide and a bone fixation device. The bone fixation device includes a plurality of screw receiving apertures extending therethrough. The drill guide includes a top face and a plurality of drill apertures extending from the top face through the drill guide. The drill apertures of the drill guide are arranged such that the drill apertures can be separated into two groups by an imaginary dividing line, and, if a separation between the two groups in the plane of the top face and normal to the dividing line were increased by a distance d, then the arrangement of the drill apertures would match, or otherwise be aligned with, that of the screw receiving apertures.

15 Claims, 8 Drawing Sheets

SURGICAL APPARATUS

CROSS-REFERENCE TO RELATED APPLICATIONS

This application claims benefit of U.S. application Ser. No. 14/812,676, entitled "SURGICAL APPARATUS," filed Jul. 29, 2015, which claims the benefit of Great Britain Patent Application No. GB1413387.0, filed on Jul. 29, 2014, which are hereby incorporated by reference in their entirety.

TECHNICAL FIELD

The present disclosure is related to a surgical apparatus and method of extending a length of a bone.

BACKGROUND

It is often desired to increase the length of a bone. This is typically achieved by cutting the bone into two portions with a bone saw. The surgeon then holds the two portions of the bone apart by a distance equal to the desired increase in length of the bone. While holding the two bone portions in position, the surgeon places a bone fixation plate against the bone, drills screw receiving recesses in the bone through screw receiving apertures in the bone fixation device, and then finally screws the bone fixation plate to the bone. This procedure requires a considerable amount of manual dexterity on the part of the surgeon, while also making the operation time consuming, thus increasing the risk of complications, such as infection. Additionally, the surgeon may require several attempts at drilling the screw receiving recesses in the correct positions in the bone, which weakens the bone.

SUMMARY

The present disclosure relates to a surgical apparatus. More particularly, but not exclusively, the present disclosure relates to a surgical apparatus comprising a bone fixation device comprising a plurality of screw receiving apertures extending therethrough and a drill guide comprising a top face and a plurality of drill apertures extending from the top face through the drill guide. The drill apertures are arranged such that the drill apertures are divided into two groups by an imaginary dividing line, such that if the two groups are separated from one another in a direction normal to the imaginary dividing line, in the plane of the top face, all of the drill apertures would be simultaneously aligned with all of the screw receiving apertures.

One aspect of the present disclosure provides a surgical apparatus comprising a combination of a drill guide and a bone fixation device. The bone fixation device includes a plurality of screw receiving apertures extending therethrough. The drill guide includes a top face and a plurality of drill apertures extending from the top face through the drill guide. The drill apertures of the drill guide are arranged such that the drill apertures can be separated into two groups by an imaginary dividing line. If a separation of a distance d between the two groups occurs, in the plane of the top face and normal to the imaginary dividing line, then the arrangement of each of the drill apertures would be aligned with each the screw receiving apertures.

The surgical apparatus according to the disclosure considerably simplifies the surgical procedure of lengthening a bone. The drill guide can be placed against the bone and recesses can be drilled in the bone through the drill apertures. The bone can then be cut where two cut ends of the bone are then separated by a distance d. Once the two cut ends of the bone are separated by the distance d, the arrangement of the recesses in the bone will match the arrangement of the screw receiving apertures of the bone fixation device. The bone fixation device can then be secured to the bone, such as with one or more screws.

The amount of dexterity required on the part of the surgeon is considerably reduced. Further, use of the surgical apparatus considerably speeds up the procedure and increases the reliability with which the surgeon can correctly drill the recesses in the bone.

At least one of the drill guide and the bone fixation device may be a plate.

The drill guide may further include a separation plate extending therefrom, where the thickness of the separation plate is equal to the distance d.

The screw receiving apertures may be arranged along a line. The screw receiving apertures may be equally spaced along the line. Alternatively, the screw receiving apertures may be unequally spaced along the line.

The surgical apparatus may include a saw guide extending from the drill guide. The saw guide may be configured to be detachable from the drill guide. The drill guide may include a first portion and a second portion, where each portion includes one drill aperture group. The first portion and the second portion may be connected to one another by a separation mechanism, configured for adjusting the separation between the two portions.

A further aspect of the disclosure provides a method of extending the length of a bone with a surgical apparatus including a drill guide and a bone fixation device. The method includes providing a surgical apparatus and positioning the drill guide against a bone. The drill guide includes a first group and a second group of drill apertures. A first group and a second group of recesses are drilled in the bone, through the respective first group and the second group of drill apertures. The bone is cut into two portions, such that each of the two portions includes a respective one of the first group and the second group of apertures. The two portions of the bone are separated from one another. A separation plate is inserted in between the two portions of the bone to separate the two bone portions from one another by a distance d. The bone fixation device is arranged on the bone, such that the first group and the second group of the screw receiving apertures are aligned with the respective first group and the second group of recesses in the bone. A fastener is inserted through each of the first group and the second group of screw receiving apertures and into the respective first group and the second group of recesses, such that the bone fixation device is attached to the bone.

Inserting the fastener may include inserting a screw through each of the first group and the second group of screw receiving apertures and into the respective first group and the second group of recesses, such that the bone fixation device is attached to the bone.

The above features and advantages and other features and advantages of the present teachings are readily apparent from the following detailed description of the best modes for carrying out the present teachings when taken in connection with the accompanying drawings.

BRIEF DESCRIPTION OF THE DRAWINGS

FIG. 1(b1) is a schematic plan view of the drill guide, illustrating an imaginary dividing line, separating the drill apertures into a first group of drill apertures and a second group of drill apertures.

FIG. 1(b2) is a schematic plan view of the drill guide and the bone fixation device, with the drill guide illustrating the first group of drill apertures spaced a distance d from the second set of apertures, if separated from one another along the imaginary dividing line, such that the drill apertures are simultaneously alignable with the screw receiving apertures of the bone fixation device.

DETAILED DESCRIPTION

Referring to the drawings, wherein like reference numbers refer to like components throughout the several Figures, a surgical apparatus 1 is shown schematically in FIG. 1. The surgical apparatus 1 comprises a drill guide 2 and a bone fixation device 3. In this embodiment both the drill guide 2 and the bone fixation device 3 are plates.

The drill guide plate 2 has a length L, width and thickness. The thickness of the plate 2 is greater than its width. The drill guide plate 2 is typically made from surgical steel or other non-deformable material. Extending from a top face 4 of the drill guide 2 through the drill guide 2 is a plurality of apertures 5.

The bone fixation device 3 comprises a plate having a plurality of screw receiving apertures 6 extending therethrough. The bone fixation device 3 is also typically comprises a surgical steel.

Figure 1:
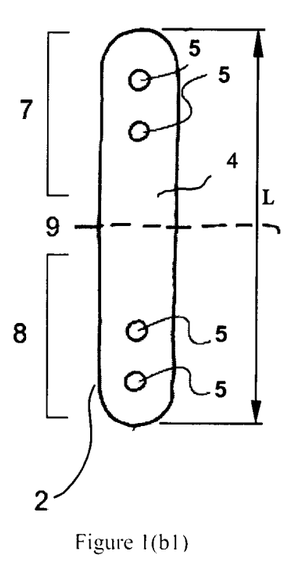
FIG. 1(a) is a schematic perspective view of a surgical apparatus including a drill guide, having drill apertures, and a bone fixation device, having screw receiving apertures.
Figure 1A:
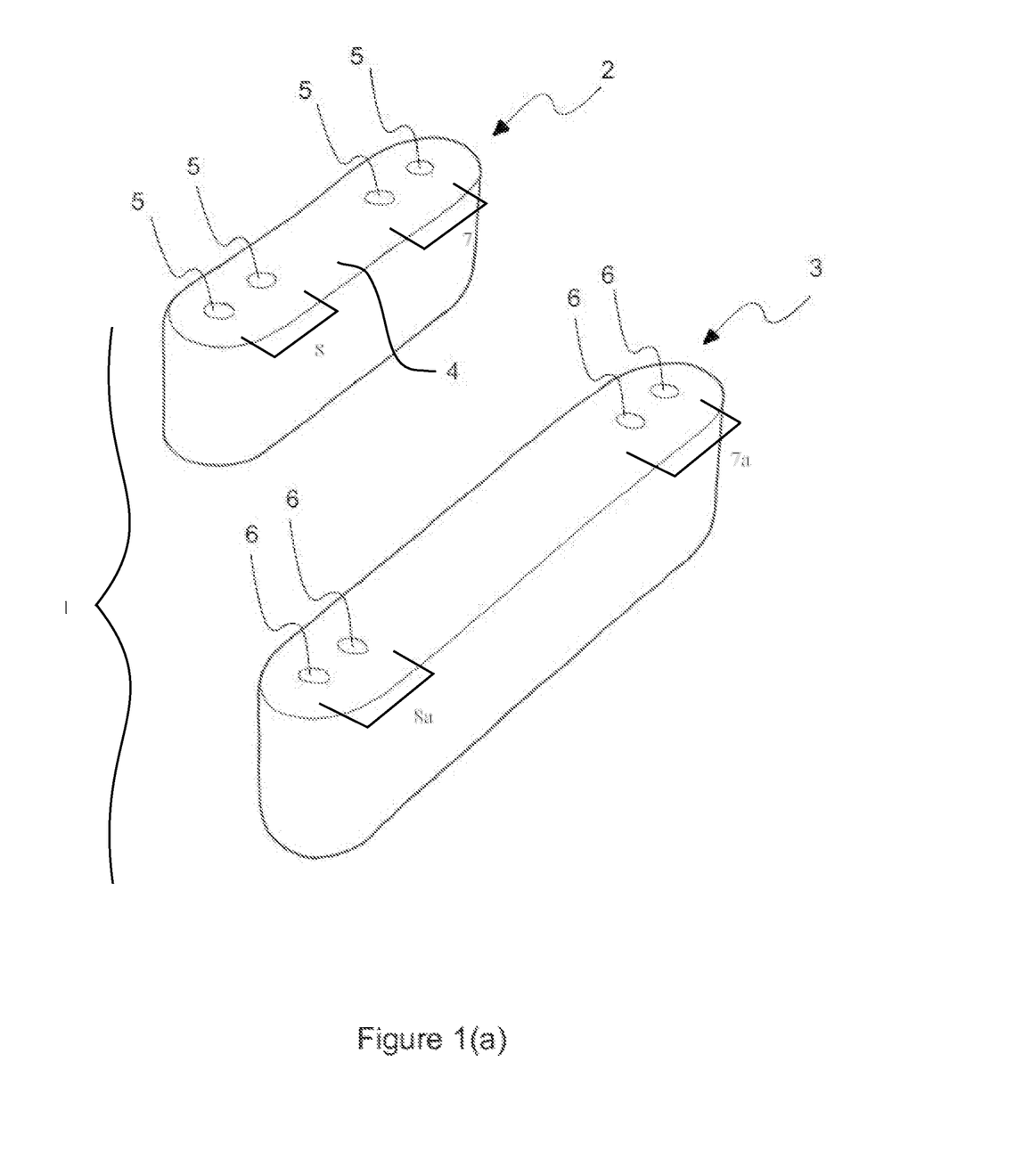

As shown in FIG. 1(b1), the drill apertures 5 can be divided into first and second groups 7, 8 by an imaginary dividing line 9. The imaginary dividing line 9 is imaginary in the sense that it provides for, or otherwise divides, the drill apertures 5 into the first and separate groups 7, 8. The imaginary dividing line 9 may be a straight line. Further, the imaginary dividing line 9 may be normal to the length L of the drill guide plate 2. As shown in FIG. 1(b2), the screw receiving apertures 6 may be dividing into a first group and a second group 7a, 7b. If a separation of a distance d between the two groups 7, 8 were to occur, in the plane of the top face 4 normal to the dividing line 9 such that the drill guide plate 2 is 'extended' (as shown in FIG. 1(b2)), then the arrangement of the drill apertures 5 would match the arrangement of the screw receiving apertures 6. In other words if one were to arrange the bone fixation plate 3 next to the 'extended' drill guide plate 2, then the two sets of apertures 5, 6 would line up (i.e., the first groups 7, 7a would be aligned with one another and the second groups 8, 8a would be aligned with one another) so that fasteners 20, such as screws, may be passed through the drill apertures 5, into the screw receiving apertures 6.

Figure 2A:
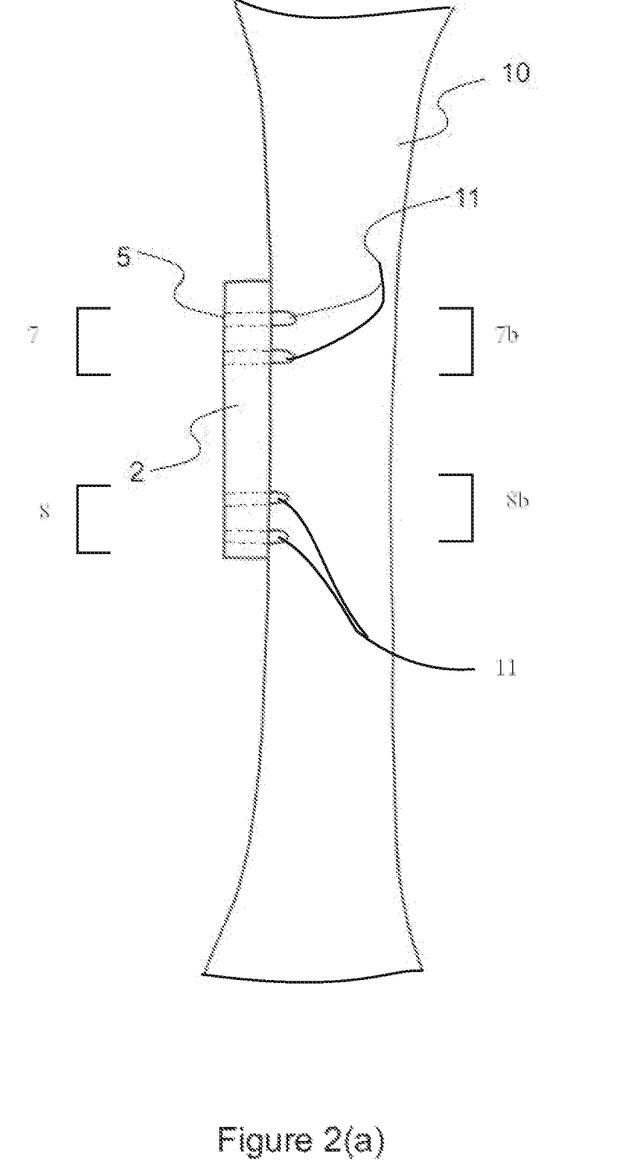
FIG. 2(a) is a schematic side view of the drill guide arranged against a bone, with recesses drilled in the bone through the drill apertures of the drill guide.
Figure 2B:
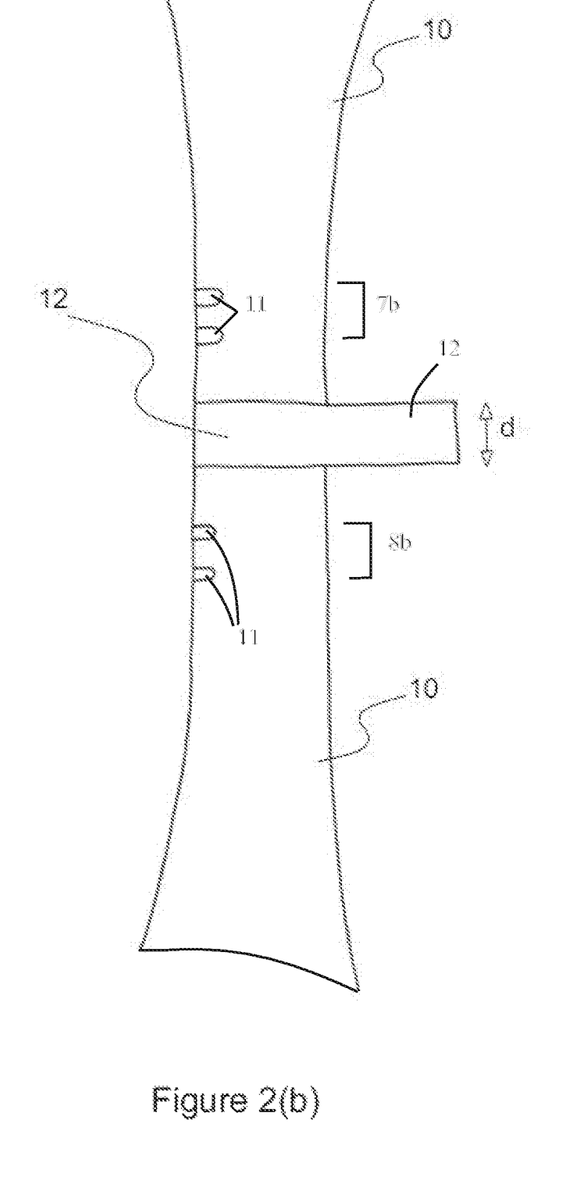
FIG. 2(b) is a schematic side view of a separation plate inserted between two cut ends of the bone.
Figure 2C:
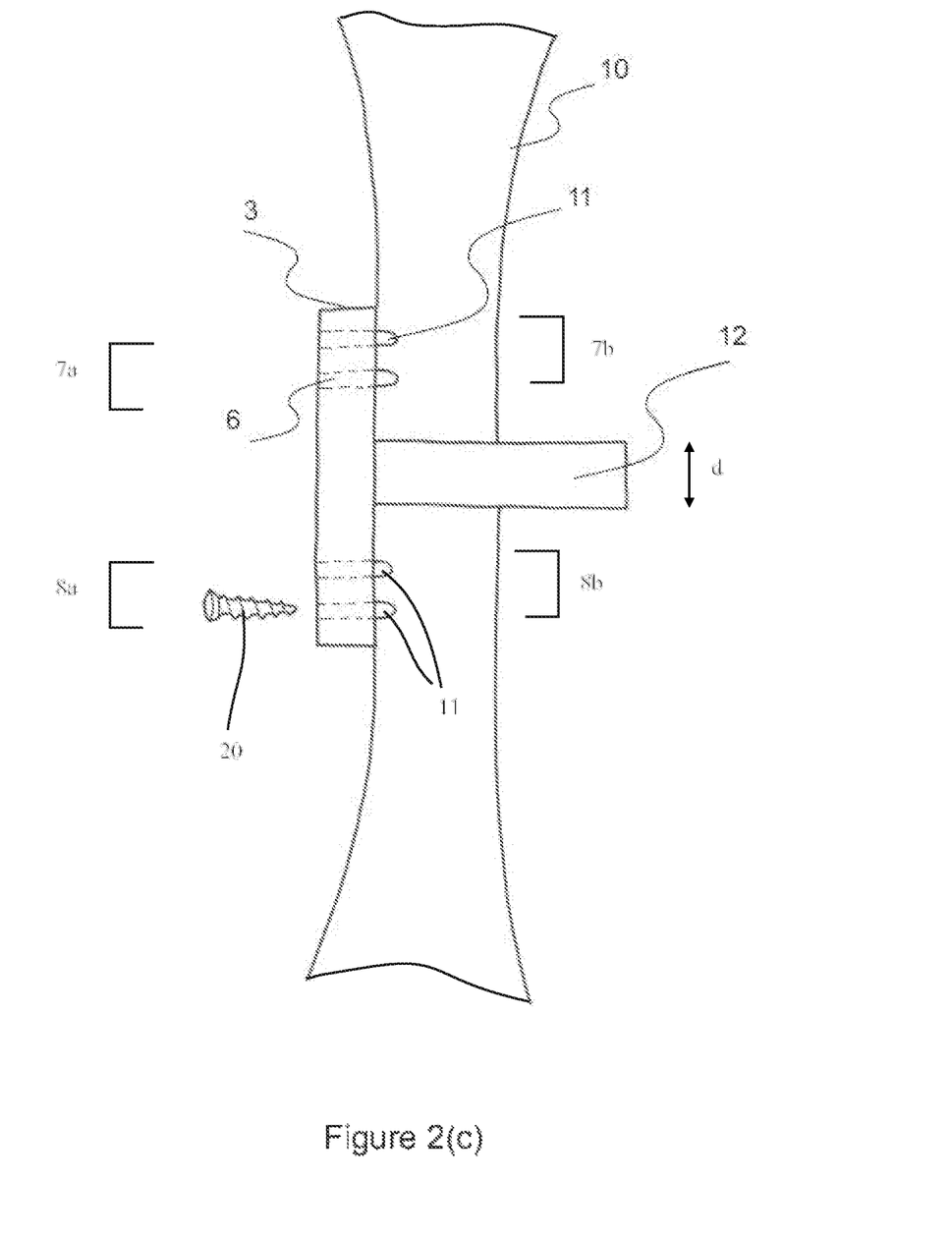
FIG. 2(c) is a schematic side view of the separation plate inserted between the two cut ends of the bone and the bone fixation plate placed against the bone, with all of the screw receiving apertures in alignment with all of the recesses in the bone, and with a screw being inserted into one of the screw receiving apertures.

FIGS. 2(a) to 2(c) show the surgical apparatus 1 according to the disclosure, in use.

In a first step (shown in FIG. 2(a)) the drill guide plate 2 is arranged against a bone 10. A surgeon drills recesses 11 in the bone 10 through the drill apertures 5. The recesses 11 may be divided into a first group and a second group 7b, 8b, corresponding to the first group 7 and the second group 8 of drill apertures 5 in the drill guide plate 2. The drill guide plate 2 is then removed before the surgeon cuts the bone 10 into two portions.

The surgeon may then insert a separation plate 12 between the two cut ends of the bone 10, thus separating the two bone portions by the thickness d of the separation plate 12. This is shown in FIG. 2(b).

In a next step, shown in FIG. 2(c), the bone fixation plate 3 is placed against the bone 10. Provided a separation plate 12 of the correct thickness t has been used, the recesses 11 in the bone 10 will be aligned with the screw receiving apertures 6 in the bone fixation plate 3. More specifically, the first group 7a of the screw receiving apertures 6 would be aligned with the first group 7b of recesses 11 and the second group 8a of the screw receiving apertures 6 would be aligned with the second group 8b of the recesses 11 in the bone 10. The bone fixation plate 3 may then be screwed to the two bone portions 10, by inserting the fasteners 20 through the aligned apertures 6 and recesses 11. Then, the separation plate 12 may be removed, completing the procedure.

Figure 3:
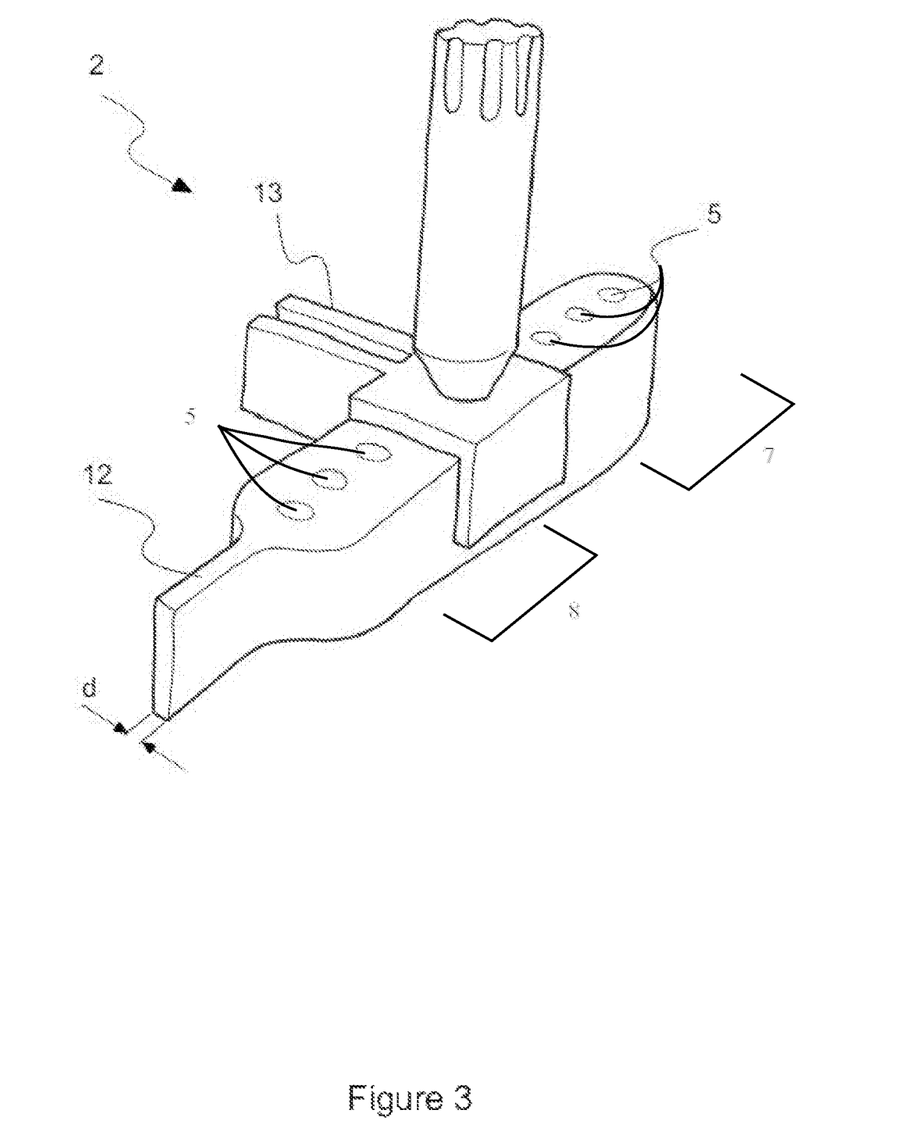
FIG. 3 is a schematic perspective view of a further embodiment of a drill guide of a surgical apparatus according to the disclosure.

Shown in FIG. 3 is an alternative embodiment of a drill guide 2 of a surgical apparatus 1 according to the disclosure. As with the embodiment of FIG. 1, the drill guide 2 is a plate with a plurality of drill apertures 5 extending through the plate 2. Connected to the plate 2 is a saw guide 13. The saw guide 13 can be removed from the drill guide plate 2 for cleaning. Further, extending from the drill guide plate 2 is a separation plate 12 which has a thickness d.

The method of use of the drill guide plate 2 of FIG. 3 is similar to that described above. In a first step, the drill guide plate 2 is placed against the bone 10 and recesses 11, drilled in the bone 10 through the drill apertures 5. Before the drill guide plate 2 is removed, however, a bone saw (not shown) is positioned in the saw guide 13. The bone saw is used to score a mark on the bone 10. The drill guide plate 2 is then removed and the surgeon cuts through the bone 10 at the score mark, dividing the bone 10 into two portions. The drill guide plate 2 is then rotated, and the separation plate 12 inserted between the two cut ends of the bone 10, separating the two bone portions 10 by a distance d. As previously explained, with reference to FIG. 2(c), the bone fixation plate 3 is then placed against the bone 10 with the screw receiving apertures 6 of the bone fixation plate 3 aligned with the recesses 11 in the bone 10. The bone fixation plate 3 can then be screwed to the bone 10 with bone fixation screws 20 before finally the separation plate 12 is removed from a gap, defined between the two cut ends of the bone 10, which are separated by the distance d.

Figure 4:
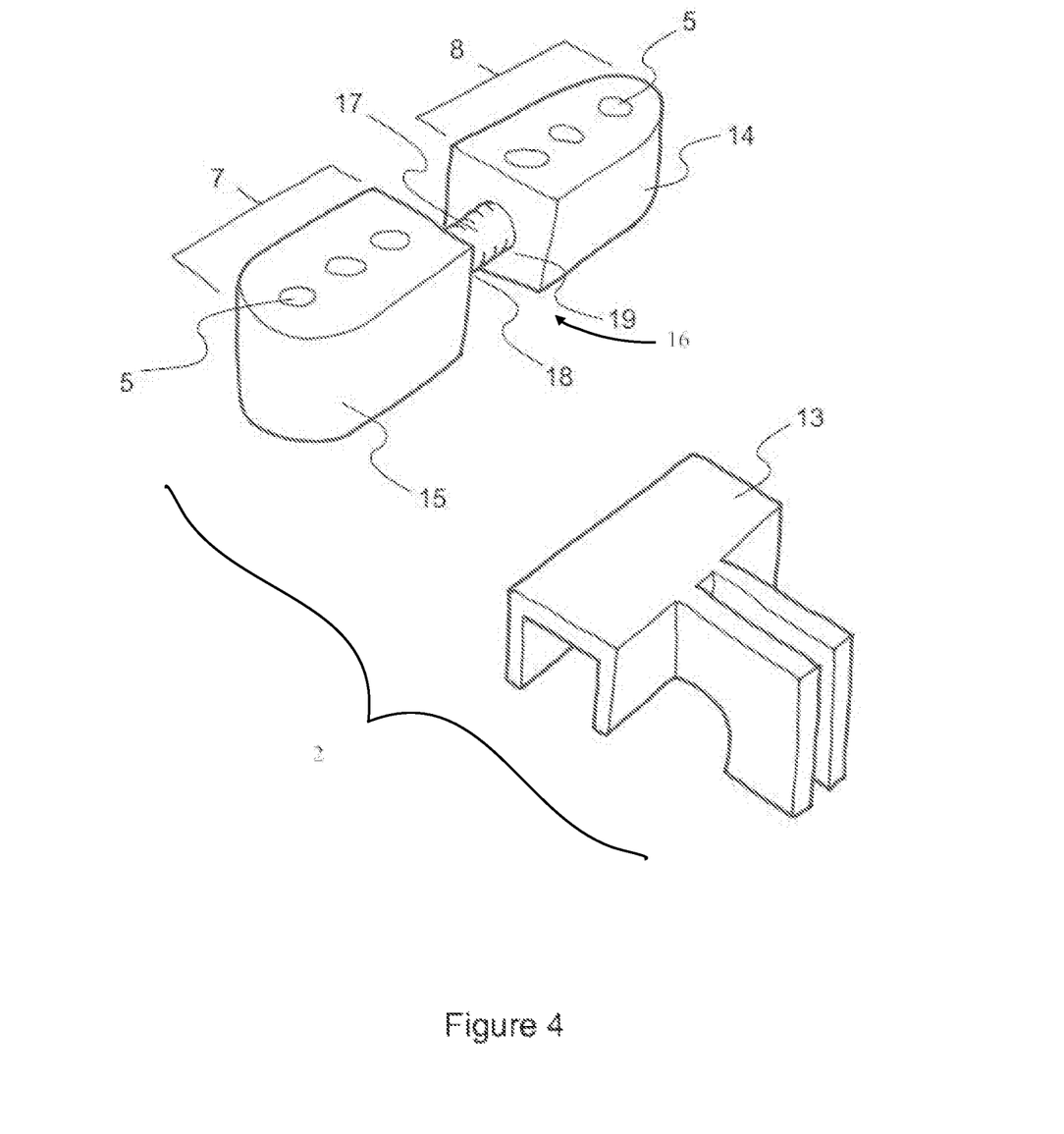
FIG. 4 is a schematic perspective view of a further embodiment of a drill guide of a surgical apparatus according to the disclosure.

Shown in FIG. 4 is a further embodiment of a drill guide 2 of a surgical apparatus 1 according to the disclosure. In this embodiment the drill guide 2 comprises first and second portions 14, 15, each of which comprises one of the groups 7, 8 of drill apertures 5. The two portions 14, 15 are connected together by a separation mechanism 16 for adjusting the separation between the two portions 14, 15. In this embodiment the separation mechanism 16 comprises a threaded rod 17. Each of the portions 14, 15 comprise a corresponding threaded aperture 18, 19, into which the rod 17 is received. Each complete turn of one of the portions 14, 15 about the rod 17 separates the two portions 14, 15 by a predetermined distance. An optional saw guide 13 can be attached to the drill guide 2.

In use, the drill guide 2 is arranged with the two portions 14, 15 abutting one another. One of the portions 14, 15 is then turned about the rod 17 until the arrangement of the drill apertures 5 matches the arrangement of the screw receiving apertures 6 of the bone fixation device 3. By counting the number of turns, the surgeon can calculate the thickness d of separation plate 12 required.

Figure 5:
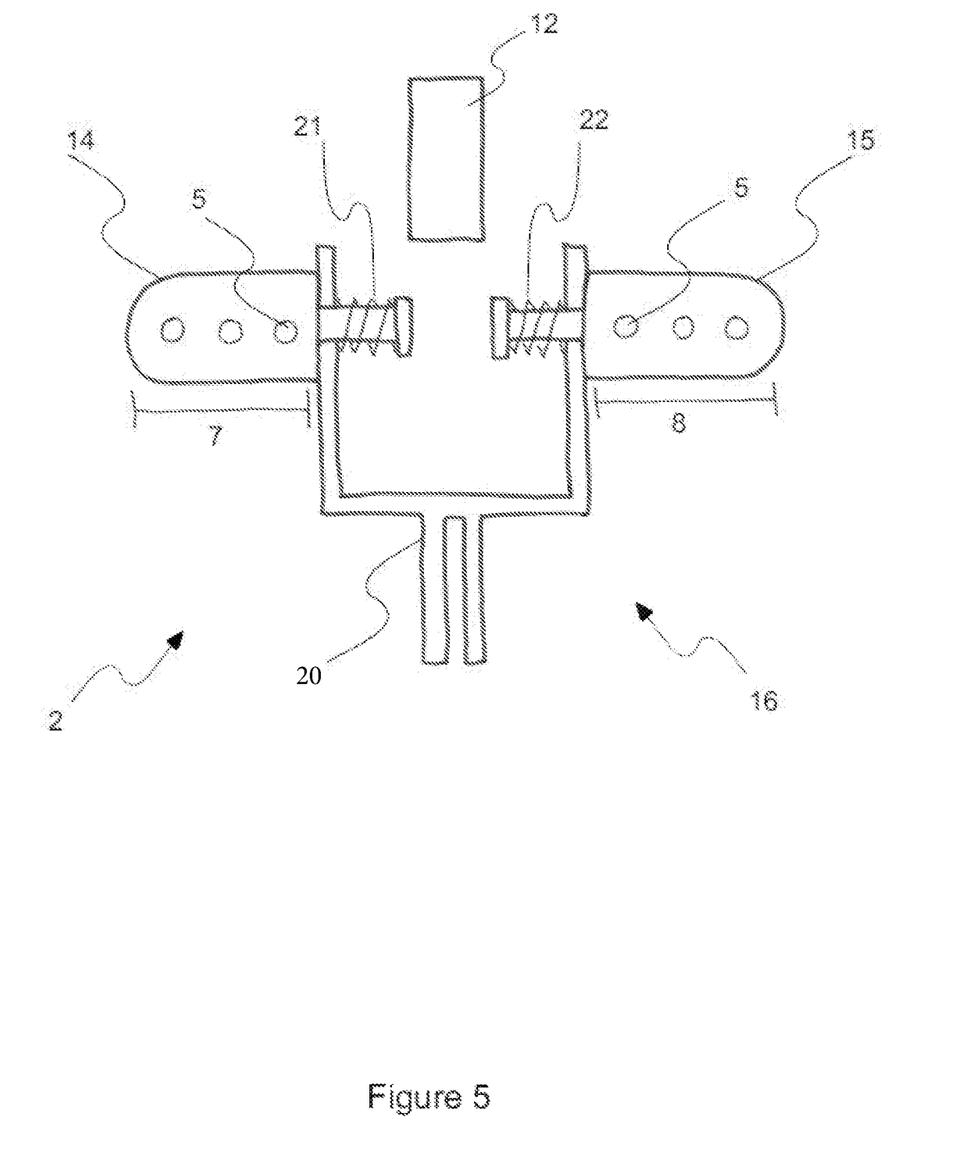
FIG. 5 is a schematic side view of a further embodiment of a drill guide of a surgical apparatus according to the disclosure.

Shown in FIG. 5 is a further embodiment of a drill guide 2 according to the disclosure. The drill guide 2 comprises first and second portions 14, 15 each having a group 7, 8 of drill apertures 5 extending therethrough. A separation mechanism 16 connects the two portions 14, 15 together. The separation mechanism 16 comprises a U shaped support 20 having first and second springs 21, 22 connected thereto. Each spring 21, 22 is connected to a respective portion 14, 15, as shown. The springs 21, 22 urge the two portions 14, 15 toward one another.

In use, separation plates 12 of different thicknesses are inserted between the two portions 14, 15 until a correct separation plate 12 is found which makes the arrangement of the apertures 5 of the drill guide 2 match the arrangement of the screw receiving apertures 6 of the bone fixation device 3 (FIGS. 1(b2) and 2(c)). The correct separation plate 12 is then removed. With the separation plate 12 removed, the two portions 14, 15 are urged toward one another under the biasing action of the springs 21, 22. The drill guide 2 is then used, as previously described herein. When the two cut ends of the bone 10 are separated, the correct separation plate 12, identified previously, is inserted therebetween.

In all of the above embodiments, the apertures 5, 6 in the drill guide plate 2 and the bone fixation device 3 are arranged along respective lines. The screw receiving apertures 6 in the bone fixation device 3 may be equally spaced. In an alternative embodiment the screw receiving apertures 6 may be unequally spaced. In alternative embodiments more complex arrangements of apertures 6 may be employed.

In the above embodiments the bone fixation device 3 is a plate. In alternative embodiment the bone fixation device 3 may be a more complex structure. For example the bone fixation device 3 may comprise a plurality of substantially spherical screw receiving members connected together by receiving arms. Each screw receiving member has a screw receiving aperture 6 extending therethrough.

While the best modes for carrying out the many aspects of the present teachings have been described in detail, those familiar with the art to which these teachings relate will recognize various alternative aspects for practicing the present teachings that are within the scope of the appended claims.

The invention claimed is:

1. A surgical apparatus comprising:
    a drill guide including a top face and a plurality of drill apertures extending from the top face through the drill guide;
    wherein the plurality of drill apertures are arranged in a first group and a second group of drill apertures, such that the first group of drill apertures may be separated from the second group of drill apertures by an imaginary dividing line; and
    a bone fixation device configured to be attached to bone, the bone fixation device including a plurality of screw receiving apertures extending therethrough;
    wherein the plurality of screw receiving apertures are arranged in a first group and a second group of screw receiving apertures; wherein the first group and the second group of drill apertures are configured such that if the first group and the second group are separated from one another by a distance, in a plane of the top face and normal to the imaginary dividing line, the first group of drill apertures are alignable with the first group of screw receiving apertures and the second group of drill apertures are simultaneously alignable with the second group of screw receiving apertures; and
    wherein the drill guide further includes a separation plate extending therefrom, wherein the separation plate has a thickness equal to the distance;
    wherein the drill guide further includes a separation plate extending therefrom,
    wherein the separation plate has a thickness equal to the distance, such that the separation plate is configured for insertion between cut bone portions.

2. The surgical apparatus as claimed in claim 1, wherein at least one of the drill guide and bone fixation device is a plate.

3. The surgical apparatus as claimed in claim 1, wherein the plurality of the screw receiving apertures are arranged along a line.

4. The surgical apparatus as claimed in claim 3, wherein the plurality of the screw receiving apertures are equally spaced along the line.

5. The surgical apparatus as claimed in claim 3, wherein the plurality of the screw receiving apertures are unequally spaced along the line.

6. The surgical apparatus as claimed in claim 1, further comprising a saw guide extending from the drill guide.

7. The surgical apparatus as claimed in claim 6, wherein the saw guide is configured to be detached from the drill guide.

8. The surgical apparatus as claimed in claim 1, wherein the drill guide includes a first portion and a second portion, wherein each of the first portion and second portions include one of the first group and the second group of drill apertures;
    wherein the first portion and the second portion are operatively connected to one another by a separation mechanism; and
    wherein the separation mechanism is configured for adjusting the distance between the two portions.

9. A surgical apparatus comprising:
    a drill guide including a top face and a plurality of drill apertures extending from the top face through the drill guide;
    a saw guide extending from the drill guide;
    wherein the plurality of drill apertures are arranged in a first group and a second group of drill apertures, such that the first group of drill apertures may be separated from the second group of drill apertures by an imaginary dividing line; and
    a bone fixation device configured to be attached to bone, the bone fixation device including a plurality of screw receiving apertures extending therethrough;
    wherein the plurality of screw receiving apertures are arranged in a first group and a second group of screw receiving apertures; and
    wherein the first group and the second group of drill apertures are configured such that if the first group and the second group are separated from one another by a distance, in a plane of the top face and normal to the imaginary dividing line, the first group of drill apertures are alignable with the first group of screw receiving apertures and the second group of drill apertures are simultaneously alignable with the second group of screw receiving apertures.

10. The surgical apparatus as claimed in claim 9, wherein the saw guide is configured to be detached from the drill guide.

11. The surgical apparatus as claimed in claim 9, wherein the drill guide includes a first portion and a second portion, wherein each of the first portion and second portions include one of the first group and the second group of drill apertures;
   wherein the first portion and the second portion are operatively connected to one another by a separation mechanism; and
   wherein the separation mechanism is configured for adjusting the distance between the two portions.

12. The surgical apparatus as claimed in claim 9, wherein at least one of the drill guide and bone fixation device is a plate.

13. The surgical apparatus as claimed in claim 9, wherein the plurality of the screw receiving apertures are arranged along a line.

14. The surgical apparatus as claimed in claim 13, wherein the plurality of the screw receiving apertures are equally spaced along the line.

15. The surgical apparatus as claimed in claim 14, wherein the plurality of the screw receiving apertures are unequally spaced along the line.

* * * * *